United States Patent [19]

Ambler

[11] 4,351,711

[45] Sep. 28, 1982

[54] ELECTROPHORESIS METHOD FOR DETECTING GLYCOSYLATED HEMOGLOBIN IN BLOOD

[75] Inventor: Jeffrey Ambler, Newthorpe, England

[73] Assignee: Gelman Sciences, Inc., Ann Arbor, Mich.

[21] Appl. No.: 256,201

[22] Filed: Apr. 21, 1981

[51] Int. Cl.³ ............................................. B01D 13/02
[52] U.S. Cl. .............................. 204/180 G; 204/180 S
[58] Field of Search ........................ 204/180 G, 180 S

[56] References Cited

U.S. PATENT DOCUMENTS 3,914,168 10/1975 Arlington ...................... 204/180 G

OTHER PUBLICATIONS

Hackh's Chemical Dictionary, 4th Ed (1969) p. 206.

*Primary Examiner*—Howard S. Williams
*Attorney, Agent, or Firm*—Reising, Ethington, Barnard, Perry & Brooks

[57] ABSTRACT

In accordance with the invention the glycosylated hemoglobin in a blood sample is electrophoretically separated from the other constituents by including dextran sulphate in the electrophoresis buffer, or by mixing a solution of the dextran sulphate with the blood sample prior to the electrophoresis, such that the blood is in contact with dextran sulphate during the electrophoresis. The presence of the dextran sulphate results in a clear and well defined electrophoretic separation of the glycosylated hemoglobin from the non-glycosylated hemoglobin, thereby enabling accurate glycosylated hemoglobin determination.

8 Claims, No Drawings

ELECTROPHORESIS METHOD FOR DETECTING GLYCOSYLATED HEMOGLOBIN IN BLOOD

TECHNICAL FIELD

The present invention relates to blood analysis for the detection of blood abnormalities and, more specifically, to a method for the electrophoretic separation of the glycosylated hemoglobin in a blood sample to enable accurate determination of the glycosylated hemoglobin level in the blood. Glycosylated hemoglobin is sometimes also referred to in the literature as the glycohemoglobins and as hemoglobin $A_I$.

BACKGROUND ART

It is already well known that a high level of glycosylated hemoglobin in human blood is a reliable indication of a blood abnormality such as in the case of a diabetic. Because the glycosylated hemoglobin level of blood at a given point in time represents a time-averaged glucose level of the blood, determination of the glycosylated hemoglobin level of a patient's blood is a more reliable indication of the average glucose level of the patient's blood over a period of time than is afforded by determination of the glucose level itself. That is, the glycosylated hemoglobin level of a patient's blood at the time a sample is taken is much less dependent on the diet of the patient immediately prior to the sample taking than is the glucose level of the blood. Hence, considerable work has been done in recent years on methods for accurately determining the amount of glycosylated hemoglobin in blood.

At present, the most commonly used method involves separation of the glycosylated hemoglobin fraction from the other hemoglobin fractions in microcolumns of ion exchange resin with subsequent measurement, spectrophotometrically, of the amount of the adsorbed fraction constituting the glycosylated hemoglobin. This method has a number of disadvantages perhaps the chief of which is that separation of the fractions is highly temperature dependent thereby requiring meticulous temperature control or other cumbersome corrections based on empirical factors and data.

It has also been proposed to accomplish the separation by electrophoresis but the difficulty here has been that of attaining a good electrophoretic separation of the glycosylated hemoglobin fraction from the non-glycosylated hemoglobin fraction—this because the fractions have very similar mobilities. In the one electrophoretic technique which is known to have come into commercial use in this regard, the separation attained is adequate; however, the technique is expensive in that it involves the use of a specially prepared agar medium including a closely controlled concentration of sulphate moieties and with the separation involving endosmosis.

The present invention provides a reliable and relatively inexpensive method for attaining electrophoretically an excellent separation of the glycosylated hemoglobin from the other hemoglobin fractions.

DISCLOSURE OF INVENTION

Most basically, what I have discovered is that an excellent separation of the glycosylated hemoglobin from the other hemoglobin fractions in blood can be attained electrophoretically by including dextran sulphate in the buffer solution used for the electrophoresis, or by mixing an aqueous solution of dextran sulphate with the blood prior to the electrophoresis, such that during the electrophoresis the blood is in contact with the dextran sulphate. It is believed that this is because the non-glycosylated hemoglobin bonds, whereas the glycosylated hemoglobin does not bond, to the dextran sulphate to the end that mobility of the non-glycosylated hemoglobin is reduced sufficiently to differ substantially from the mobility of the glycosylated hemoglobin. But whatever the explanation, it has been found that by formulating the electrophoresis buffer to include dextran sulphate, or by mixing the dextran sulphate with the blood sample prior to the electrophoresis, uniformly excellent separations of the glycosylated hemoglobin from the other hemoglobin fractions can be attained relatively simply and at low cost using a conventional agar, cellulose or other support medium for the separation and using electrophoresis equipment of conventional construction.

The invention will be described in detail chiefly with reference to the preferred embodiment wherein the dextran sulphate is included in the buffer solution.

The concentration of the dextran sulphate is not critical but because a high concentration is not necessary, it is advantageous to use only a small amount so as to minimize costs. The amount used need only be sufficient to effect a change in the relative mobilities of the glycosylated and non-glycosylated hemoglobin fractions sufficiently to accomplish the desired separation. The preferred concentration for the dextran sulphate in the buffer solution is from 0.01% to 0.2% by weight, though lower or higher concentrations can be used, the latter particularly where the same solution without replenishment is to be used for a number of the electrophoretic separations. A concentration of 0.03% by weight is excellent. Likewise, the molecular weight of the dextran sulphate is not critical except that it has been found that a molecular weight in excess of about 500,000 is disadvantageous in that it can cause undesired interference with mobility. The preferred molecular weight range for the dextran sulphate is from about 5,000 to 100,000. That having a molecular weight of about 8,000 is excellent.

The buffer solution must, of course, be electrically conductive and contain a buffer to maintain the pH within the 5.5 to 7.5 range conventionally used for electrophoresis on blood, the preferred pH range for the practice of the present invention being from about 6 to 7. Citric acid—citrate in a concentration of from about 0.25 to 1 moles per liter citrate ion to provide the preferred pH of from 6 to 7, is excellent though other buffers, for example acetate or phosphate, can be used. The citrate or other buffer ion provides the solution its electrical conductivity. If additional ionic content is desired for this purpose, it can be supplied by a minor addition of salt such as sodium chloride, though such is generally not required.

BEST MODE FOR CARRYING OUT THE INVENTION

The most preferred buffer solution is a 0.05 molar aqueous citric acid-sodium citrate solution buffering same to a pH of about 6.3 and containing 0.03% by weight dextran sulphate, molecular weight about 8,000. Such solution can be made by dissolving, per liter of water, 0.3 grams of the dextran sulphate, 14.1 grams trisodium citrate and sufficient citric acid, about 0.6 grams, to adjust the pH to about 6.3. As specific examples of other buffers, there can be used trisodium phosphate in a like amount, i.e. 14 grams per liter (with adjustment to the desired pH by phosphoric acid), or a like amount of sodium acetate (with adjustment to the pH by acetic acid). The amount of buffer used is not critical, it only being necessary that the pH be maintained as desired and that the solution have sufficient ionic content to provide the electrical conductivity required for the electrophoresis. Whatever the buffer, from about 0.25 to 1 moles per liter, just as stated above for the citrate, is generally preferred though lesser or greater amounts can be used.

The electrophoresis apparatus used for the practice of the method can be of conventional construction well known in the art and commonly used for the electrophoretic separation of blood or other protein material into its constituents of different mobilities. The medium or substrate for the blood sample on which the separation is performed can, for example, be agarose gel or cellulosic material, such as cellulose acetate membrane conventionally used as the medium for electrophoretic separations. For simplicity and low cost, a cellulosic membrane is preferred. If it is desired to use agarose gel there is no requirement for special formulation but instead it can be that conventionally used for the electrophoretic separation of proteins having different mobilities.

As blood sample treatment, the blood sample can be diluted 1:2 with a hemolyzing reagent, e.g. 20 ul blood into 40 ul reagent, a typical hemolyzing reagent being an aqueous solution of 0.1% by weight saponin and 0.05% by weight disodium salt of ethylene diamine tetraacetic acid. The so-diluted sample is stable up to 1 week at 4° C. Other hemolyzing reagents well known in the art, or just distilled water, can be used to dilute the blood sample as desired.

Where a cellulosic membrane is used as the medium, as is preferred, it is soaked in the buffer solution in a conventional manner until fully saturated and the diluted blood sample, typically about 0.25 to 0.5 ul thereof, is placed on the soaked membrane and the membrane then placed in the electrophoresis chamber containing the buffer solution which can be at room temperature. Electrophoresis is then carried out, typically for 40 minutes at 150 volts (initial current 5–6 mAmp; final current 8–9 mAmp). At the conclusion of the electrophoresis the membrane, with the blood sample thereon which has now been separated into its fractions, is removed from the chamber and, after conventional blotting, is placed in a conventional fixative solution, typically 6% by weight trichloracetic acid and 2.5% by weight formaldehyde, for about 2 minutes. It is then transferred to a conventional washing solution, typically 5% by weight acetic acid solution, for 5 minutes after which it is blotted and dried. The separated fractions are then quantitated using conventional techniques and equipment, for example, a densitometer. After the samples are prepared, the entire procedure takes only about one hour. Cellulose acetate or cellulose nitrate membrane, particularly the latter, is excellent as the medium for the practice of the invention.

It will be understood that while the above specific example and procedure constitute the best manner now known for the practice of the invention (providing a separation of the glycosylated hemoglobin from the non-glycosylated hemoglobin in about 0.4 mm center-to-center bands, which provide excellent quantitative results) various changes and modifications can be made. The cardinal feature, essential to the good results, is that of including dextran sulphate in the buffer solution in a small but effective amount to effect the change in the comparative mobilities of the glycosylated and non-glycosylated hemoglobin during the electrophoresis thereby providing a clear and distinct electrophoretic separation thereof and enabling subsequent accurate quantitation of the separated glycosylated hemoglobin fraction. To exemplify the procedural changes which can be made, fixation of the separated fractions on the membrane can be eliminated if desired. This has the advantage of slightly lessening the time required for the procedure; but the quantitative results are generally not as reliable and accurate, probably because of band diffusion. As an addition to the procedure, the separated fractions can be stained with a protein dye prior to quantitation. The voltage, current density, duration, solution temperature and other conditions used in the electrophoresis procedure can be as conventionally used in electrophoretic procedures on blood, the conditions recited above being typical. Ingredients in addition to the dextran sulphate and buffer can be used in the buffer solution if desired, so long as they do not inhibit the solution in performing its function as described. The previously mentioned sodium chloride is one example and, as another example, a small amount of ethylene diamine tetraacetic acid, frequently used in buffer solutions for the electrophoresis of blood, can be included if desired.

As has been stated earlier herein, instead of including the dextran sulphate in the buffer solution, the dextran sulphate can be mixed with the blood sample prior to the electrophoresis. For example, the dextran sulphate, preferably in an amount of from 0.01% to 0.2% by weight can be included in the hemolyzing reagent with which the blood sample is diluted such that the blood sample placed on the medium for the electrophoresis already contains and hence is in contact with the dextran sulphate. The entire electrophoresis procedure can otherwise be the same as described above except, of course, that the buffer solution need not be formulated to include the dextran sulphate.

It will be understood that while the invention has been described specifically with reference to preferred embodiments thereof, various changes and modifications may be made all within the full and intended scope of the claims which follow.

What is claimed is:

1. A method for electrophoretically separating glycosylated hemoglobin from non-glycosylated hemoglobin in a blood sample, said method comprising placing a medium with the blood sample thereon in a buffer solution, and then passing an electric current through said solution to cause the blood to separate on said medium into fractions having different mobilities, the buffer solution which is in contact with the blood sample containing dextran sulphate to effect a change in the relative mobilities of the glycosylated hemoglobin and the non-glycosylated hemoglobin fractions in the blood whereby the glycosylated hemoglobin is separated from the non-glycosylated hemoglobin during passage of the electric current.

2. A method as set forth in claim 1 wherein the dextran sulphate has a molecular weight of from about 5,000 to 100,000.

3. A method as set forth in claim 1 wherein the buffer solution has a pH of from about 6 to 7.

4. A method as set forth in claim 1 wherein the solution contains citrate as buffer.

5. A method as set forth in claim 1 wherein the dextran sulphate is included in the buffer solution prior to placing therein said medium with the blood sample thereon.

6. A method as set forth in claim 5 wherein the dextran sulphate is present in the buffer solution in an amount from about 0.01% to 0.2% by weight and has a molecular weight of from about 5,000 to 100,000.

7. A method as set forth in claim 1 wherein the dextran sulphate is mixed with the blood sample prior to placing the blood sample on the medium.

8. A method as set forth in claim 7 wherein the blood sample is mixed with an aqueous solution containing from about 0.01% to 0.2% dextran sulphate having a molecular weight of from about 5,000 to 100,000.

* * * * *